United States Patent [19]

Gander et al.

[11] 4,126,699

[45] Nov. 21, 1978

[54] RETINOIC ACID DERIVATIVES FOR THE TREATMENT OF ACNE

[75] Inventors: Robert J. Gander, Whitehouse; John A. Gurney, East Brunswick, both of N.J.

[73] Assignee: Johnson & Johnson, New Brunswick, N.J.

[21] Appl. No.: 822,286

[22] Filed: Aug. 5, 1977

Related U.S. Application Data

[62] Division of Ser. No. 628,185, Nov. 3, 1975, Pat. No. 4,055,659.

[51] Int. Cl.² .................... A61K 31/215; C11C 3/02

[52] U.S. Cl. .................... 424/305; 260/410.6
[58] Field of Search ............ 260/410.6, 410; 424/305

[56] References Cited

U.S. PATENT DOCUMENTS

| 2,951,853 | 9/1960 | Matsui et al. ............ 260/410.9 M |
| 3,950,418 | 4/1976 | Bollag et al. ............ 260/557 R |

*Primary Examiner*—V. D. Turner

[57] ABSTRACT

Esters and amides of all-trans-retinoic acid are disclosed which are useful for the treatment of acne.

9 Claims, No Drawings

RETINOIC ACID DERIVATIVES FOR THE TREATMENT OF ACNE

CROSS-REFERENCE TO RELATED APPLICATION

This application is a division of our copending application Ser. No. 628,185, filed Nov. 3, 1975, now U.S. Pat. No. 4,055,659, issued Oct. 25, 1977.

BACKGROUND OF THE INVENTION

Retinoic acid is known to be useful for the treatment of acne. See, for example, U.S. Pat. No. 3,729,568, which discloses the use of retinoic acid compositions for the treatment of acne. Side effects associated with the use of retinoic acid, such as, for example, excessive erythema, have stimulated efforts to discover other acne treatment materials which would not have these side effects.

In order to discover such materials, the well-known ability of retinoic acid to promote increased epidermal DNA synthesis upon topical application was utilized. This ability has been associated with the effectiveness of retinoic acid in the treatment of acne. See, for example, Christophers and Braun-Falco: *Stimulation of Epidermal DNA-Synthesis with Vitamin A-Acid,* Arch. Klin. exp. Derm. 232: 427–433 (1968) and Wolfe, et al.: *Changes in Epidermal Differentiation After Vitamin A Acid,* Arch. Klin. exp. Derm. 237: 744–795 (1970). Forty-eight novel esters and amides of all-trans-retinoic acid have been prepared and tested for their efficacy in promoting increased epidermal DNA synthesis.

SUMMARY OF THE INVENTION

This invention relates to esters and amides of all-trans-retinoic acid and more particularly to those esters and amides having the formula:

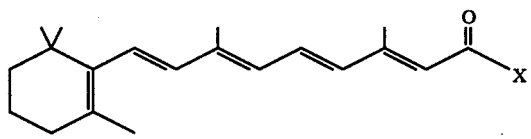

wherein X is a member selected from the group consisting of: —OCH$_2$CONH$_2$; mixed—OCH$_2$CH(OH)CH$_3$ and —OCH(CH$_3$)CH$_2$OH; —OCH$_2$CH$_2$OH;

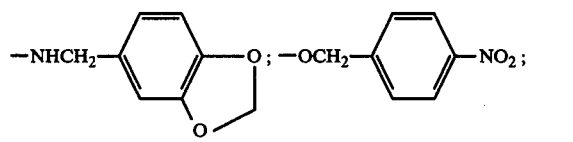

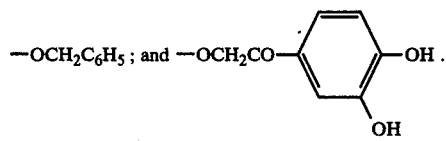

It has surprisingly been discovered that only these seven novel compounds, of the 48 novel compounds prepared and tested, are active in the following test measuring DNA synthesis and therefore are useful for the treatment of acne. Further, these seven novel compounds generally do not produce the excessive erythema characteristic of retinoic acid. While it is believed that these compounds are useful for the treatment of acne, it is also suggested that they are useful for treatment or amelioration of the same additional classes of skin disorders as is retinoic acid itself. These disorders include ichthyoses (e.g., ichthyosis hystrix, epidermolytic hyperkeratosis, and lamelar ichthyosis), follicular disorders (e.g., pseudofolliculites, senile comedones, nevus comidonicus, and trichostatis spinulosa), benign epithelial tumors (e.g., flat warts, trichoepithelioma, and molluscum contagiosum), perforated dermatoses (e.g., elastosis perforans serpiginosa and Kyrle's disease), and disorders of keratinization (e.g., Darier's disease, keratoderma, hyperkeratosis plantaris, pityriasis rubra pilaris, lichen planus, acanthosis nigricans, and psoriasis).

Ten male guinea pigs (Hartley strain) weighing ca. 400 g each were used for each compound to be tested. The animals were housed singly in wire cages, handled daily during experimentation, provided chow and water ad libitum, and maintained on 12/12 hour light/dark cycles. Prior to the experimental procedure, the animals were maintained as just described for 3 days.

On the first day of the test, one ear (dorsal skin) of each animal was randomly selected and treated with 0.025 ml of the experimental solution, and the other ear was treated with an equal volume of the placebo vehicle (control). Ten animals for each compound were so treated. These topical applications were made at 9:00 am on the first 4 days of the experiment. All the animals received chronic administration of tritiated thymidine ($^3$H-TdR) for these first 4 days. The $^3$H-TdR was given intraperitoneally at about 9:30 am, 1:30 pm and 5:00 pm of each day (10 micro Curie in 0.1 ml H$_2$O/injection; specific activity = 2.0 Curie/millimole). On the fifth day (9:00 am), the animals were killed, and 6 mm diameter punches of ear skin from the central portion of the treated sites were harvested.

Each of these tissue samples was solubilized at 37°–50° C. for 13 days in 1 ml of an alkali solubilizer sold by Amershan-Searle Co. under the registered trademark "NCS" Solubilizer. The dissolved tissues kept in nylon scintillation vials were acidified with 0.025–0.050 ml of acetic acid, and diphenyloxazole in toluene was added as a fluor to detect the beta particles emitted by absorbed tritiated thymidine. The radioactivity of the samples was determined by multiple counting on a Beckman LS counter. All count per minute values were quench corrected by external standardization to yield disintegrations per minute (dpm)/6 mm punch of skin. Quench correction is especially important as some of the samples show faint yellow coloration due to the presence of the retinyl derivative, and therefore present considerable color quench.

The test compounds were applied as dilute solutions (0.05%–0.2%) in 50:50 parts by weight propylene glycol-ethanol or 35:35:30 parts by weight propylene glycol-ethanol-chloroform. The compounds of the invention provoke thymidine uptake significantly greater than the control at greater than 90% confidence level and generally at greater than 99% confidence level. The test results for the compounds of the invention are shown in Table I, to which results for unsubstituted all-trans-retinoic acid are added for comparison.

TABLE I

| COMPOUND | DPM (standard error) | Confidence Level |
|---|---|---|
| 0.05% all-trans-retinoyloxyacetamide | 2360(408) | 90% |
| Control | 1779(211) | |
| 0.05% mixed 2-hydroxy-1-propyl and 1-hydroxy-2-propyl-all-trans-retinoates | 1672(152) | 99% |
| Control | 1259(91) | |
| 0.2% 2-hydroxyethyl-all-trans-retinoate | 12945(1669) | 99.9% |
| Control | 3416(947) | |
| 0.2% N-(3,4-methylenedioxyphenylmethyl)-all-trans-retinamide | 11,186(2266) | 99% |
| Control | 2862 | |
| 0.2% 4-nitrobenzyl all-trans-retinoate | 13910(1252) | 99.9% |
| Control | 1906(158) | |
| 0.2% benzyl all-trans-retinoate | 14168(2346) | 99% |
| Control | 2006(418) | |
| 0.05% 4-(all-trans-retinoyloxyacetyl)-catechol | 2116(275) | 99% |
| Control | 1230(83) | |
| 0.05% all-trans-retinoic acid | 4429(912) | 99% |
| Control | 1504(147) | |

Surprisingly, only these seven compounds of the 48 novel compounds tested gave positive results on this test and hence are useful for the treatment of acne. The compounds of the invention may be topically applied to the acne site in any suitable pharmaceutically acceptable vehicle, as for example a liquid carrier such as propylene glycol-ethanol, propylene glycol-ethanol-chloroform, and the like. A preferred liquid composition is a solution of a small amount of at least one of the compounds of the invention in a combination of (A) from about 25% to about 75% by weight of 95% ethanol and (B) from about 75% to about 25% by weight of a liquid glycol. A typical solvent carrier of this type comprises 50% by weight 95% ethyl alcohol and 50% by weight propylene glycol. The preferred concentration of the active compound in these compositions is at least about 0.01% by weight, more preferably from about 0.01% to about 0.5% by weight, and most preferably from about 0.5% to about 0.2% by weight, but any therapeutically effective concentration may be used. This method of use is the same as taught in the above-mentioned U.S. Pat. No. 3,729,568, the contents of which are incorporated herein by reference. These compositions and the method of treating acne by topical application to the acne site of at least one of the compounds of the invention are also considered part of the present invention.

The 41 novel esters and amides of all-trans-retinoic acid which were inactive in the above test are listed below:
2-Cyclohexylethyl all-trans-Retinoate
10-Carbomethoxydecyl all-trans-Retinoate
4-Hydroxybutyl all-trans-Retinoate
Cholesteryl all-trans-Retinoyloxyacetate
Cholesteryl all-trans-Retinoate
Mixed m- and p-vinylbenzyl all-trans-Retinoates
4-Bromobenzyl all-trans-Retinoate
all-trans-Retinoyloxyacetylbenzene
4-(all-trans-Retinoyloxyacetyl)-bromobenzene
4-(all-trans-Retinoyloxyacetyl)-methoxybenzene
4-(all-trans-Retinoyloxyacetyl)-nitrobenzene
4-(all-trans-Retinoyloxyacetyl)-phenol
4-(all-trans-Retinoyloxyacetyl)-toluene
4-(all-trans-Retinoyloxyacetyl)-benzonitrile
4-(all-trans-Retinoyloxyacetyl)-ethoxybenzene
4-(all-trans-Retinoyloxyacetyl)-acetoxybenzene
4-(all-trans-Retinoyloxyacetyl)-naphthalene
4-(all-trans-Retinoyloxyacetyl)-biphenyl
all-trans-Retinoyloxyacetyl-2,5-dimethoxybenzene
all-trans-Retinoyloxyacetyl-2,4-dichlorobenzene
all-trans-Retinoyloxyacetyl-2,4-dimethylbenzene
all-trans-Retinoyloxyacetyl-3,4-diacetoxybenzene
all-trans-Retinoyloxyacetyl-3,4,5-trimethoxybenzene
all-trans-Retinoyloxyacetyl-2,4,6-trimethylbenzene
N-n-Propyl all-trans-retinamide
N-tert-Butyl all-trans-retinamide
N-(1,1,3,3-tetramethyl)-butyl all-trans-retinamide
N-(all-trans-Retinoyl)-morpholine
4-(all-trans-Retinoyl)-aminophenol
Methyl 4-(all-trans-Retinoylamino)-salicylate
N,N'-Dicyclohexyl-N-(all-trans-retinoyl)-urea
Acetone (all-trans-Retinoyl)-hydrazone
trans-$\beta$-Ionone (all-trans-Retinoyl)-hydrazone
N-(all-trans-Retinoyl)-imidazole
N-(all-trans-Retinoyloxy)-succinimide
N-(all-trans-Retinoyloxy)-phthalimide
1-Nicotinoyl-2-(all-trans-retinoyl)-hydrazine
1-(all-trans-Retinoyl)-benzotriazole
1-(all-trans-Retinoyl)-1,2,4-triazole
N-[$\beta$-(3,4-Dimethoxyphenyl)ethyl]-all-trans-retinamide
2-(all-trans-Retinoylamino)-benzothiazole These 41 inactive compounds are the subject of our U.S. patent application entitled "Retinoic Acid Derivatives," Ser. No. 628,177 filed on Nov. 3, 1975.

The preparation of the compounds of the present invention is illustrated by the following examples.

EXAMPLE I all-trans-RETINOYLOXYACETAMIDE

In a 1000 ml three-necked round-bottom flask equipped with reflux condenser, stirrer, and nitrogen inlet were placed ethyl acetate (500 ml), all-trans-retinoic acid (10 g; 0.30 mole), anhydrous potassium carbonate (4.6 g, 0.30 mole), 2-chloroacetamide (30 g, 0.32 mole) and sodium iodide (5.0 g, 0.30 mole). This mixture was stirred at reflux temperature for 18 hours under nitrogen atmosphere.

At the end of the 18-hour period, the mixture was cooled to room temperature and extracted with three 500-ml portions of water, three 500-ml portions of 10% sodium carbonate in water, and one 500-ml portion of water. After each extraction the upper layer was retained and the lower layer discarded.

The final upper layer was dried over anhydrous magnesium sulfate, filtered, and the filtrate evaporated under reduced pressure, leaving an orange oil. The oil was dried at ambient temperature and 0.5 mm pressure, causing it to turn to an orange-yellow solid, melting at 62°-64° C.

The crude product was recrystallized from hot toluene yielding pure all-trans-retinoyloxyacetamide, melting at 133°–134° C. The proton magnetic resonance spectrum of the compound was consistent with the structure written.

Anal. Calcd. for $C_{22}H_{31}NO_3$: C, 74.4; H, 8.2; N, 3.9. Found: C, 74.4; H, 8.5; N, 3.9.

EXAMPLE II

MIXED 2-HYDROXY-1-PROPYL and 1-HYDROXY-2-PROPYL all-trans-RETINOATES

A U.S.P. grade propylene glycol (1,2-propanediol) was used in this preparation. A solution of 6 ml of propylene glycol and 3 ml of pyridine in 10 ml of benzene reacted readily when added during about three minutes to a solution of retinoyl chloride (which had been prepared from 3.0 g of all-trans-retinoic acid and phosphorous trichloride in 25 ml of benzene according to directions of Huisman, et al., Rec. trav. chim., 75, 977-1006 (1956)). The reaction was moderated at or below room temperature with a Dry Ice - isopropanol bath. The reaction mixture was stirred magnetically under a nitrogen atmosphere at room temperature for an hour, during which time the reaction flask was kept covered with aluminum foil.

The golden-yellow reaction solution was diluted with 20 ml of ethyl ether and washed with two 20-ml portions of 2% hydrochloric acid, with 20 ml of 10% aqueous sodium bicarbonate solution, and finally with 20 ml of 10% saturated sodium chloride solution. The washed benzene-ether solution was dried over anhydrous magnesium sulfate.

The solution was then placed on 75 ml of activated alumina in a chromatography column. The column was eluted with 2 liters of ethyl ether, the composition of the eluates being monitored by thin layer chromatography. Impurities were eluted in the early fractions. Later fractions containing product were combined, and the solvent was evaporated in a rotary evaporator under vacuum. The residue was a yellow oil which was crystallized from n-hexane to yield a solid. Two recrystallizations gave yellow plates, melting point 91°–95° C. The ultraviolet absorption spectrum measured in isopropanol showed a maximum at 353 nm. The proton magnetic resonance spectrum indicated the mixed isomers, ca. 70% 2-hydroxypropyl-all-trans-retinoate and ca. 30% 1-hydroxypropyl-all-trans-retinoate.

Anal. Calcd. for $C_{23}H_{33}O_3$: C, 77.2; H, 9.30. Found: C, 77.2; H, 9.47.

EXAMPLE III

2-HYDROXYETHYL all-trans-RETINOATE

A solution of retinoyl chloride was prepared from 3.0 g of all-trans-retinoic acid and 0.92 g of phosphorous trichloride in 25 ml of benzene. This solution was added gradually to a solution of 6 ml of ethylene glycol and 8 ml of pyridine during a period of 40 minutes. The moderate reaction exotherm was controlled by cooling the reaction flask in an ice bath. The reaction was then stirred under a nitrogen atmosphere for 30 minutes longer.

The orange reaction mixture was placed directly on 80 ml of activated alumina in a chromatographic column, and the column was eluted with 1.4 liters of anhydrous ethyl ether. The ether was evaporated and the residual yellow oil was applied to the top of a fresh column of 80 ml of alumina. This column was eluted successively with 1 liter of ether and 0.5 liter of ethyl acetate. Composition of the eluate was monitored by thin layer chromatography.

Evaporation of the latter fractions yielded a crude yellow crystalline product. Recrystallization, first from 5 ml n-hexane, then from 10 ml 95:5 n-hexane-benzene gave yellow plates, melting point 108°–110° C. The proton magnetic resonance spectrum verified the structure of the compound.

Anal. Calcd. for $C_{22}H_{32}O_3$: C, 76.7; H, 9.37. Found: C, 76.7; H, 9.28.

EXAMPLE IV

N-(3,4-METHYLENEDIOXYPHENYLMETHYL)-all-trans-RETINAMIDE

A solution of retinoyl chloride was prepared by magnetically stirring 3.00 g of all-trans-retinoic acid and 0.92 g of phosphorous trichloride for two hours in 50 ml of dry benzene. During 18 minutes the retinoyl chloride was added to a solution of 7.55 g of piperonylamine in 10 ml of anhydrous ethyl ether while stirring under a nitrogen atmosphere and cooling in an ice bath. Stirring was then continued for 3 hours at room temperature, and for an hour more at 50° C.

The reaction mixture was diluted with 250 ml of ethyl ether. The ether solution was extracted with two 25-ml portions of 5% hydrochloric acid, then washed with four 25-ml portions of cold water. After drying of the washed solution over sodium sulfate, the solvent was evaporated leaving 3.65 g of a sticky yellow solid. The solid hardened to a crystalline material when triturated with 50 ml of petroleum ether (b.p. 30°–60° C.). The crystals were filtered, washed with 25 ml of petroleum ether, and vacuum dried at room temperature to yield crude product. This product was recrystallized twice from methanol (5 ml per gram) giving pure compound, melting point 106°–107° C. The proton magnetic resonance spectrum was consistent with the structure with no extraneous resonances.

Anal. Calcd. for $C_{28}H_{35}NO_3$: C, 77.6; H, 8.14; N, 3.23. Found: C, 77.6; H, 8.15; N, 3.31.

EXAMPLE V

4-NITROBENZYL all-trans-RETINOATE

Potassium retinoate was made by neutralizing 3.00 g of all-trans-retinoic acid in 30 ml of tetrahydrofuran with 15.6 ml of 0.640 N methanolic potassium hydroxide. The solvent was evaporated on a rotary evaporator and the residue dried at a pressure of less than 0.5 mm. for several hours.

Powdered potassium retinoate (3.03 g) in 20 ml of hexamethylphosphoramide was stirred overnight at room temperature with 2.16 g of 4-nitrobenzyl bromide. The reaction mixture was poured into 30 ml of cold 5% hydrochloric acid, precipitating a bright-yellow gum. The gum was washed by decantation with 60 ml of cold water, then was dissolved in 300 ml of ethyl ether. The ether solution was washed with four 40-ml portions of ice water and dried over sodium sulfate. Evaporation of the ether left a bright-yellow powder.

The material was recrystallized twice from 50:50 chloroform-methanol (6 ml per gram), giving tiny, bright-yellow prisms, melting point 130°–131° C. The proton magnetic resonance spectrum was consistent with the structure.

Anal. Calcd. for $C_{27}H_{33}NO_4$: C, 74.4; H, 7.63; N, 3.22. Found: C, 74.3; H, 7.73; N, 3.14.

EXAMPLE VI

BENZYL all-trans-RETINOATE

Powdered potassium retinoate (3.03 g) in 20 ml of hexamethylphosphoramide was stirred overnight at room temperature with 1.26 g of benzyl chloride. The reaction mixture was poured into 30 ml of cold 5% hydrochloric acid, precipitating an oil which was then taken up in 150 ml of ethyl ether. The solution was washed with four 25-ml portions of ice water and dried over sodium sulfate. Evaporation of the ether left a residue of yellow semi-solid. This residue was triturated with 50 ml of petroleum ether (b.p. 30°-60° C.) and chilled in ice. The solution was filtered from a little retinoic acid, and the filtrate was then evaporated to about 5 ml volume.

A chromatography tube 16 × 180 mm was filled to a depth of 125 mm with chromatographic silica gel, 40-140 mesh. The petroleum ether solution (5 ml) was put on the column and the chromatogram developed with 50:50 benzene-petroleum ether by volume. Material coming off the column was monitored by thin layer chromatography on silica gel plates using 70:30 benzene-n-hexane developer and iodine vapor visualization. Evaporation of the purest fractions gave a mobile, clear, yellow oil.

The whole preparation was repeated and the product combined with the 1.50 g from the first preparation. The combined material was chromatographed again as before. The residue after evaporation of the solvent was dried by rotating it on a rotary evaporator at 0.2 mm for 4 hours. The compound was a clear yellow liquid which exhibited the correct proton magnetic resonance spectrum and elemental analysis.

Anal. Calcd. for $C_{27}H_{34}O_2$: C, 83.0; H, 8.77. Found: C, 83.3; H, 8.89.

EXAMPLE VII

4-(all-trans-RETINOYLOXYACETYL)-CATECHOL

Powdered potassium retinoate (3.03 g) and 1.86 g of α-chloro-3′,4′-dihydroxyacetophenone in 22 ml of hexamethylphosphoramide were stirred overnight at 40°-45° C. The reaction mixture was poured into 30 ml of cold 5% hydrochloric acid, precipitating a thick yellow gum. The acid was decanted, and the gum was triturated with 30 ml of distilled water. The gum was then dissolved in 150 ml of ethyl ether and washed with four 25-ml portions of cold water. The ether solution was evaporated, leaving a dry, yellow powder.

The powder was recrystallized twice from 3:1 methanol-water by volume (42 ml per gram). Product was a yellow-green powder, melting point 177°-178° C. The proton magnetic resonance spectrum was consistent with the structure.

Anal. Calcd. for $C_{28}H_{34}O_5$: C, 74.6; H, 7.61. Found: C, 74.0; H, 7.48.

The following example illustrates the use of the compounds of the invention. All parts are by weight.

EXAMPLE VIII

| A liquid vehicle consisting of: | Parts |
|---|---|
| 95% ethyl alcohol | 500 |
| propylene glycol | 500 | is prepared by mixing the ingredients together. To the resulting vehicle is added 2 parts of 2-hydroxyethyl-all-trans-retinoate, and the whole is thoroughly mixed until the active ingredient is dissolved. The resulting composition is useful for the treatment of acne by periodic topical application to the acne site. Application generally should be made at least once daily for at least 1 month.

The above examples have been provided to illustrate the present invention, the scope of which is defined by the following claims.

What is claimed is:

1. Mixed 2-hydroxy-1-propyl all-trans-retinoate and 1-hydroxy-2-propyl all-trans-retinoate.

2. A pharmaceutical composition for the treatment of acne by topical application which comprises an effective acne-treatment amount of mixed 2-hydroxy-1-propyl all-trans-retinoate and 1-hydroxy-2-propyl all-trans-retinoate.

3. The composition of claim 2 wherein the mixed 2-hydroxy-1-propyl all-trans-retinoate and 1-hydroxy-2-propyl all-trans-retinoate comprises from about 0.01% to about 0.5% by weight of the composition.

4. The composition of claim 3 wherein the mixed 2-hydroxy-1-propyl all-trans-retinoate and 1-hydroxy-2-propyl all-trans-retinoate comprises from about 0.05% to about 0.2% by weight of the composition.

5. The composition of claim 2 wherein the vehicle is a mixture selected from the group consisting of propylene glycol-ethanol and propylene glycol-ethanol-chloroform.

6. A method for treatment of acne in a subject requiring such treatment which comprises topical application to the acne site of said subject of a composition comprising an effective acne-treatment amount of mixed 2-hydroxy-1-propyl all-trans-retinoate and 1-hydroxy-2-propyl all-trans-retinoate.

7. The method of claim 6 wherein the mixed 2-hydroxy-1-propyl all-trans-retinoate and 1-hydroxy-2-propyl all-trans-retinoate comprises from about 0.01% to about 0.5% by weight of the composition.

8. The method of claim 7 wherein the mixed 2-hydroxy-1-propyl all-trans-retinoate and 1-hydroxy-2-propyl all-trans-retinoate comprises from about 0.05% to about 0.2% by weight of the composition.

9. The method of claim 6 wherein the vehicle is a mixture selected from the group consisting of propylene glycol-ethanol and propylene glycol-ethanol-chloroform.